US009395371B2

(12) United States Patent
Chan et al.

(10) Patent No.: US 9,395,371 B2
(45) Date of Patent: Jul. 19, 2016

(54) SYNTHESIS OF FLUORESCENT NOBLE METAL NANOPARTICLES

(76) Inventors: Warren Chan, Toronto (CA); Steven Perrault, Toronto (CA); Leo Chou, Toronto (CA)

(*) Notice: Subject to any disclaimer, the term of this patent is extended or adjusted under 35 U.S.C. 154(b) by 124 days.

(21) Appl. No.: 13/825,771

(22) PCT Filed: Sep. 23, 2011

(86) PCT No.: PCT/CA2011/001080
§ 371 (c)(1),
(2), (4) Date: Mar. 22, 2013

(87) PCT Pub. No.: WO2012/037667
PCT Pub. Date: Mar. 29, 2012

(65) Prior Publication Data
US 2013/0183665 A1 Jul. 18, 2013

Related U.S. Application Data

(60) Provisional application No. 61/386,107, filed on Sep. 24, 2010.

(51) Int. Cl.
| | |
|---|---|
| *B82Y 40/00* | (2011.01) |
| *B82Y 30/00* | (2011.01) |
| *B82Y 5/00* | (2011.01) |
| *G01N 33/58* | (2006.01) |
| *A61K 33/24* | (2006.01) |
| *B22F 1/00* | (2006.01) |
| *C22C 5/02* | (2006.01) |
| *G01N 33/533* | (2006.01) |

(52) U.S. Cl.
CPC .............. *G01N 33/587* (2013.01); *A61K 33/24* (2013.01); *B22F 1/0018* (2013.01); *B82Y 5/00* (2013.01); *B82Y 30/00* (2013.01); *C22C 5/02* (2013.01); *G01N 33/533* (2013.01)

(58) Field of Classification Search
None
See application file for complete search history.

(56) References Cited

U.S. PATENT DOCUMENTS

| | | | | |
|---|---|---|---|---|
| 6,207,831 | B1 * | 3/2001 | Auer et al. | 544/371 |
| 6,214,560 | B1 * | 4/2001 | Yguerabide et al. | 506/3 |
| 2004/0235016 | A1 * | 11/2004 | Hamers et al. | 435/6 |
| 2008/0305489 | A1 * | 12/2008 | Thomas et al. | 435/6 |

OTHER PUBLICATIONS

Pierrat et al, Nano. Lett., vol. 7, pp. 259-263 and Supplemental Material (2007).*
Abdelhalim et al (J. Nanomed. Nanotech., vol. 3, pp. 1-5).*
Schmid, Gunter (ED). Clusters and Colloids: From Theory to Application, 1994, VCH, Weinheim.
Ahmadi, Temer S. et al., Shape-Controlled Synthesis of Colloidal Platinum Nanoparticles, Science, Jun. 28, 1996, p. 1924-1926, v272, No. 5270, American Association for the Advancement of Science.
Henglein, A. et al., Absorption Spectrum and Some Chemical Reactions of Colloidal Platinum in Aqueous Solution, J. Phys. Chem, 1995, p. 14129-14136, vol. 99, No. 38, American Chemical Society.
Curtis, Andrew C. et al., Preparation and Structural Characterization of an Unprotected Copper Sol, J. Phys. Chem., 1988, p. 2270-2275, vol. 92, No. 8, American Chemical Society.
Gentry, Stuart T. et al., Controlled Particle Growth of Silver Sols through the Use of Hydroquinone as a Selectrive Reducing Agent, Langmuir, 2009, p. 2613-2621, vol. 25, No. 5, American Chemical Soceity.
Cason, Joanna P. & Roberts, Christopher B., Metallic Copper Nanoparticles Synthesis in AOT Reverse Miccelles in Compress Propane and Supercritical Ethan Solutions, J. Phys. Chem. b. 2000, p. 1217-1221, vol. 104, No. 6, American Chemical Society.
Massart, Rene, Preparation of Aqueous Magnetic Liquids in Alkaline and Acidic Media,IEEE Transactions on Magnetics, Mar. 1981, p. 1247-1248, vol. mag-17, No. 2, IEEE.

* cited by examiner

*Primary Examiner* — Robert T Crow
(74) *Attorney, Agent, or Firm* — Eduardo Krupnik; Miller Thomson LLP

(57) ABSTRACT

A process for the production of fluorescent nanoparticles selected from noble metal or silica nanoparticles. Noble metals or silica nanoparticles provide a platform to which fluorophores and other detection molecules can be added. The fluorescent nanoparticles can be used as regents, diagnostic assays and in the tracking or targeting of tumors.

6 Claims, 2 Drawing Sheets

SYNTHESIS OF FLUORESCENT NOBLE METAL NANOPARTICLES

CROSS-REFERENCE TO RELATED APPLICATIONS

This application is a national phase application under 35 U.S.C. §371 of International Application No. PCT/CA2011/001080, filed Sep. 23, 2011, which priority to U.S. Provisional Application No. 61/386,107 filed Sep. 24, 2010. The contents of the referenced applications are incorporated by reference into the present application.

FIELD

A process for the synthesis of fluorescent noble metal, in particular gold nanoparticles over the range of 4-300 nm is described. These particles have advantageous properties, including the ability to produce a wide range of particle sizes, highly stable particles both in vitro and in vivo, and the ability to use a variety of organic dyes (for example, any Alexa Fluor dye). The fluorescent nanoparticles may be used as a reagent in many different applications, including in vitro cell labelling, in vitro diagnostic assay labelling, and in vivo tracking or tumor targeting.

BACKGROUND

Nanomaterials containing noble metals are commonly used in biological and medical applications. For example, nanomaterials containing gold or silver are commonly injected into animals as delivery vehicles for drug targeting to diseased tissues. While these nanomaterials have favourable properties for biomedical applications such as the production of heat, the scattering of light, and high surface area-to-volume ratio, they are difficult to measure and detect in a biological system. Typically, destructive techniques such as inductively-couple plasma atomic emission spectroscopy is used for analyzing nanomaterials containing noble metals. Therefore, a primary drawback of using noble metal containing nanomaterials at a size of 5 nm and above in biology and medicine is the lack of fluorescence emission. Furthermore, the design of noble-metal containing nanomaterials with fluorescence is also limited because of the quenching effects of noble metals on the fluorophores. For example, the adsorption of an organic dye molecule (alexa-fluoro 750) will be quenched when they are in contact with the surface of the noble metal.

SUMMARY

This description provides a process for the production of fluorescent-noble metal containing nanoparticles which comprises:
(1) Providing a platform of nanoparticles;
(2) Covering the surfaces of the nanoparticles to saturation with thiol-terminated polymers by one of the following methods:
 1. mixing the nanoparticles with methoxy-(polyethylene glycol)-thiol and biotin-(polyethylene glycol)-thiol;
 2. coordinating thiol and biotin thiol to the surfaces of the nanoparticles by a non-covalent bond; and
 3. directly conjugating methoxy-thiol and biotin-thiol to the surfaces of the nanoparticles,
so that the polymers bind to the surfaces of the particles as a brush layer via the thiol ends so that the biotin or methoxy ends are free; and (3) Homogeneously mixing the resulting biotin nanoparticles with fluorescent avidin or a derivative thereof in proportions such that the final concentration is 1 biotin molecule for every 10 to 1000 avidin molecules in the fluorescent multi-coloured nanoparticle-avidin complexes, each being capable of having a different targeting molecule, and which may be mixed with biotin related targets, and the fluorescent labeled avidin or a derivative thereof being spaced away from the particle surface, thus reducing or removing the potential quenching of the dye.

Nanoparticles (with a diameter of between 1-100 nm) provide a platform, to which many different fluorophores and other detection molecules can be added. A method has been optimized to construct a fluorescent nanoparticle that allows many fluorophores to bind to a single particle. Using a highly specific combination of reagents, the process also allows targeting molecules e.g., antibodies, peptides, or aptamers to be included, allowing the fluorescent nanoparticles to bind specifically to the desired target.

This approach has several advantages:
1.) Many fluorophores can be bound to a single target, increasing the sensitivity of detection.
2.) The present approach attaches multiple targeting molecules (i.e. antibodies) to a single particle. This improves the overall ability of that fluorescent nanoparticle to specifically bind and hold its target.
3.) Using the same method, it is possible to prepare fluorescent nanoparticles with many different fluorophores (many different fluorescence colours), and as many different targeting molecules (different antibodies for different targets). This allows for true multiplex capability with a single protocol.
4.) Attachment of fluorescent dyes to a metallic nanoparticle surface, if designed properly, causes further enhancement of the fluorescent signal (increased brightness).

The present synthesis protocol produces enhancement, which further improves sensitivity of detection.

DETAILED DESCRIPTION

Nanoparticle Platform

To exemplify the present process, gold nanoparticles were used as a platform. These were synthesized using a technique whereby a gold chloride solution was mixed with a specific number of gold nanoparticle "seeds" (12 nm diameter particles synthesized by the classic sodium citrate reduction method), and then hydroquinone was added as a specific reducing agent to cause reduced gold in solution to deposit on the nanoparticle seeds, thus growing them to the desired size.

Alternative metallic nanoparticle materials can be used, including but not limited to silver, platinum, palladium, copper, and rhodium. The primary role of the nanoparticle is to provide a surface on which other materials can be added. Such alternative nanoparticles are commercially available from numerous vendors.

"Nanoparticles" useful in the practice of the invention include all those consisting of noble metals such as gold, silver, platinum, palladium, copper, and rhodium, as well as silica and polymer. The size of the nanoparticles is preferably from about 1 nm to about 400 nm (mean diameter), more preferably from about 5 to about 50 nm, most preferably from about 10 to about 30 nm. The nanoparticles may also be non-spherical such as rods. Other nanoparticles useful in the invention include silica and polymer (e.g. latex or polystyrene) nanoparticles.

Methods of making metal nanoparticles are well-known in the art. See, e.g., Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988), Gentry S. T. et al, Langmuir, 25, 2613 (2009), Cason J. P. et al, Journal of Physical Chemistry B, 104, 1217 (2000). However, these methods yield somewhat heterogeneous nanoparticles and each method may have limited nanoparticle size ranges.

The term "antibody or antibodies" refers to an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular molecule is maintained.

Surface Conjugation

The nanoparticle surface may be covered to saturation with any substance capable of stabilizing the nanoparticle surface, forming a "brush" type layer on the outer surface, and containing biotin on the peripheral termini. This could be a polymer, for example poly-(ethylene glycol) (PEG), a nucleic acid, or a peptide or protein. Additionally, these substances could be mixed in different ratios on the particle surface, or a single substance without biotin could be mixed with the same substance with biotin. For example, two derivatives of PEG could be used, methoxypoly(ethylene glycol)-thiol (mPEG-SH) (molecular weight about 10,000 amu) and biotinpoly (ethylene glycol)-thiol (molecular weight about 10,000 amu). The two polymers may be mixed with the gold nanoparticles, after which the polymers bind to the particle surface as a brush layer via thiol-gold co-ordination. This means the thiol end of the polymer is attached to the nanoparticle surface, while the methoxy or biotin ends are presented outwardly to the solution. This allows the biotin to bind with avidin, streptavidin or neutravidin (or any other derivative or modification of avidin) molecules that are added into the solution. In the present description, the particle platform was optimized for use with fluorescently labelled streptavidin.

The goal of the first approach is that fluorescent gold nanoparticles are created by the direct adsorption of fluorescently-labeled PEG onto the surface of the nanoparticle. The surface can also contain a population of fluorescently-labeled PEG and/or biotin or oligonucleotide-labeled PEG. The purpose of the fluorescence is for detection and the purpose of the biotin or oligonucleotide is for tagging to other biological molecules. These molecules can be bound to the surface of the gold nanoparticles through thiol chemistry.

The goal of this approach is to provide a) a biomolecule on the particle surface that can be bound by a recognition molecule (biotin and streptavidin), b) to provide a very high degree of stability to the particle surface, and c) to space the fluorescently labelled streptavidin away from the particle surface, thus reducing or removing potential quenching of the dye. Alternatively, the PEG polymer could be replaced by any other polymer that performs the same tasks. These polymers could be either coordinated to the particle surface via a non covalent bond such as the thiol-gold interaction, or via a direct conjugation for polymer-based particles.

The percentage of the particle surface covered by methoxy versus biotin-PEG-SH depends on the size of the particle and the density of fluorescently labelled streptavidin after binding. The number of streptavidins coated onto the nanoparticle surface was optimized to ensure the surface is not saturated (ie density of protein is too high) with strepatavidin as this would cause self-quenching and would prevent the use of this technology in fluorescence applications.

The macromolecule streptavidin is actually a homotetramer, with each tetramer having the capacity to bind 4 biotin molecules. Addition of streptavidin into a solution of nanoparticles covered with biotin may therefore have the following outcomes:

1.) A single streptavidin molecule binds 4 biotins on a single nanoparticle, and will be unable to bind any further biotin molecules; or
2.) A single streptavidin molecule binds biotin molecules on 2-4 nanoparticles, cross-linking those particles and being unable to bind any further biotin molecules; or
3.) A single streptavidin molecule binds 1-3 biotin molecules on a single nanoparticle, but does not become saturated, because the number of streptavidins in solution far outnumbers the available biotins. The streptavidin molecules are therefore still able to bind further biotin molecules.

Assembly

As described above, there are a number of different possible outcomes from mixing fluorescently labelled streptavidin with biotin-coated nanoparticles. The present process was optimized to produce outcome (3), as this outcome allows additional biotinylated molecules (i.e. antibodies) to be added into the solution to bind to the gold nanoparticle-streptavidin construct. Optimization of the assembly process appears to be highly specific, and will not function correctly otherwise. The details of the synthesis protocol and assembly are as follows.

1. Density of Biotin-PEG-SH on the Nanoparticle Surface.

The density of biotin-PEG-SH on the particle determines i) how many streptavidins can be bound, ii) whether dye self-quenching occurs due to high density, and iii) what manner of biotin-streptavidin binding occurs, due to the spatial organization of available biotins.

2. Homogeneous Mixing of the Biotin-GNP and Fluorescent Streptavidin

Fluorescently labeled streptavidin must be added to the biotin-GNP mix in a manner that favors outcome 3) described above. The relative concentrations of the two reagents, the volumes of mixing, and the method of mixing were optimized.

3. Homogeneous Mixing of the GNP-Streptavidin Constructs and Biotinylated Antibodies.

Similar to the above, once GNP-streptavidin complexes have been formed, biotin-labeled targeting molecules (i.e. antibodies) can be added, which will complex with the GNP-streptavidin. The proportions of molecules needed to favour no cross-linking of particles were optimized by targeting molecules with multiple biotins. This included optimizing the volume and concentration of the biotin-targeting molecule added, and the method of mixing.

EXAMPLES

The following examples are included to illustrate, but not to limit the invention.

Overview

The experiments performed to optimize the steps above evolved through two different analytical phases. In (1) and (2) above, changes in the fluorescent signal on particles, and also for shifts in their electrophoretic mobility were primarily studied. Gel electrophoresis combined with fluorescent and while light imaging were conducted to quantify the success of these optimization steps. In (3), the primary concern was whether successful binding biotin-labeled biomolecules to the particle surface had been obtained. To visualize this, gel electrophoresis was used to first look for a shift in electrophoretic mobility, and then to test for specific binding of the constructs to targets and non-targets by adsorbing target and non-target molecules onto the surface of ELISA plates (as per normal protocols), incubated the particles with the adsorbed molecules, washed off excess and unbound constructs, and imaged for specificity and signal intensity. For protein targets, the enzyme-linked immunosorbent assay (ELISA) is the standard detection technique. The ELISA is an extremely general technique which relies on target-specific antibody labelling and calorimetric readout based either on fluorophores or chromophores.

BRIEF DESCRIPTION OF THE DRAWINGS

The present invention is further described by the accompanying figures wherein.

OPTIMIZING THE AVAILABLE BIOTIN BINDING SITES ON THE NANOPARTICLES

Figure 1:
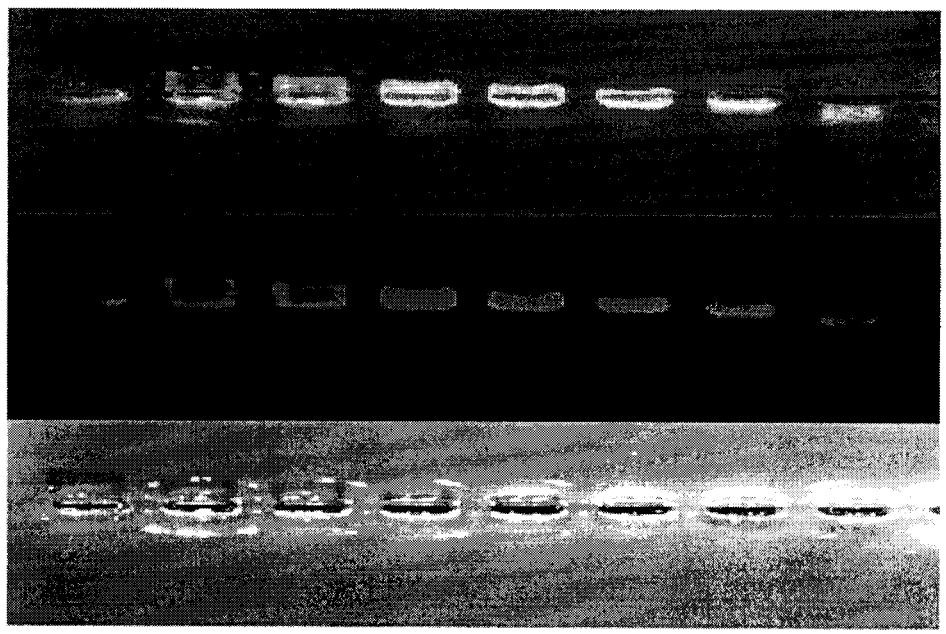
FIG. 1 illustrates an electrophoretic gel that shows electrophoretic mobility (EB) and fluorescence signal (FI) in a biotin-density dependent manner, which includes a top panel that is an overlay of fluorescence and white light, a middle panel that is fluorescence only, and the bottom panel that is white light showing absorbance and migration of the gold nanoparticles.

The number of binding sites on the surfaces of the particles determines not only how many streptavidins can be bound, but also the manner of streptavidin binding (see above). The range of biotin concentrations on the particle surface, and the ability of streptavidin binding were examined. The PEG's were mixed with the particles at different ratios, excess was washed off, and then electrophoretic mobility (EM) and fluorescence signal (Fl) in a biotin-density dependent manner were examined. Referring to FIG. 1, the top panel is an overlay of fluorescence and white light, the middle is fluorescence only, and the bottom panel is white light showing absorbance and migration of the gold nanoparticles. Left to right, is high to low density of biotin-PEG on the particles surface (from 5× biotin-PEGs added per $nm^2$ to 0.04 per $nm^2$). This shows how the migration of the particles changes depending on the number of streptavidin bound, due to the change in size and charge. It also shows that the signal increases to a maximum at approximately 0.6× biotin-PEG. As biotin density increases beyond this ratio, the density of streptavidin increases on the nanoparticle surface to the point that self-quenching from the dye occurs.

In the above example and with other similar experiments conducted, the relationship between the density of biotin-PEG on the particle surface and the brightness of the resulting particles were examined. These studies were, however, conducted without first investigating the effect of the homogeneous mixing of streptavidin-A750 and particles or whether the streptavidin that bound to the particle could bind additional biotin-labelled biomolecules.

After characterizing the above, the amount of biotin-PEG on the particle surface that would allow streptavidin binding in a manner that didn't cause cross-linking of the particles by streptavidin binding, and that would allow biotin-labelled biomolecules to bind the streptavidin was assessed. We determined by this characterizing the effect of different biotin densities binding to streptavidin, washing unbound streptavidin, binding to biotinylated biological molecules, and finally analyzing using gel electrophoresis (where we are looking for shifts in the gel to indicate the differential binding between different binding densities and the streptavidin).

Figure 2:
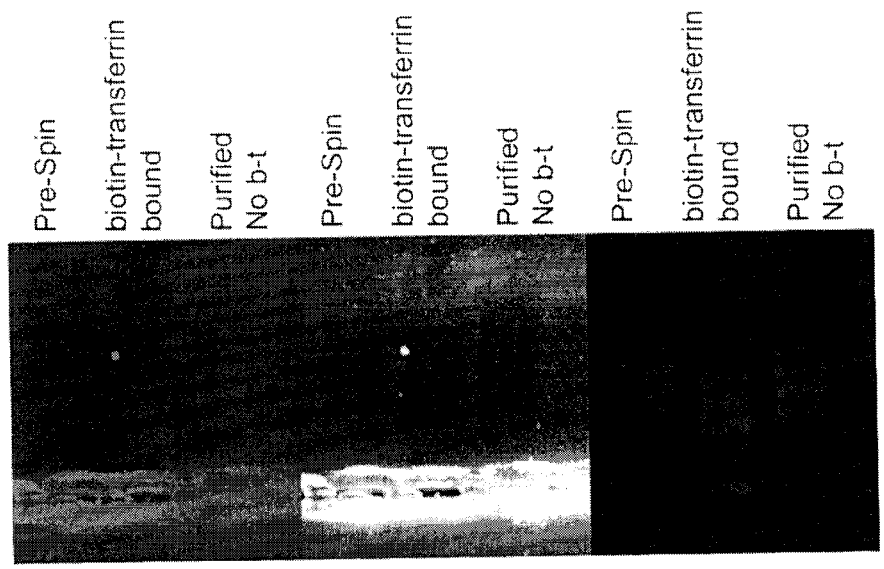
FIG. 2 illustrates an electrophoretic gel conducted to test gel shift by migration. From left to right are the fluorescence and white light overlay, then the white light only showing migration of the particles, and finally the fluorescence only channel.
Figure 3:
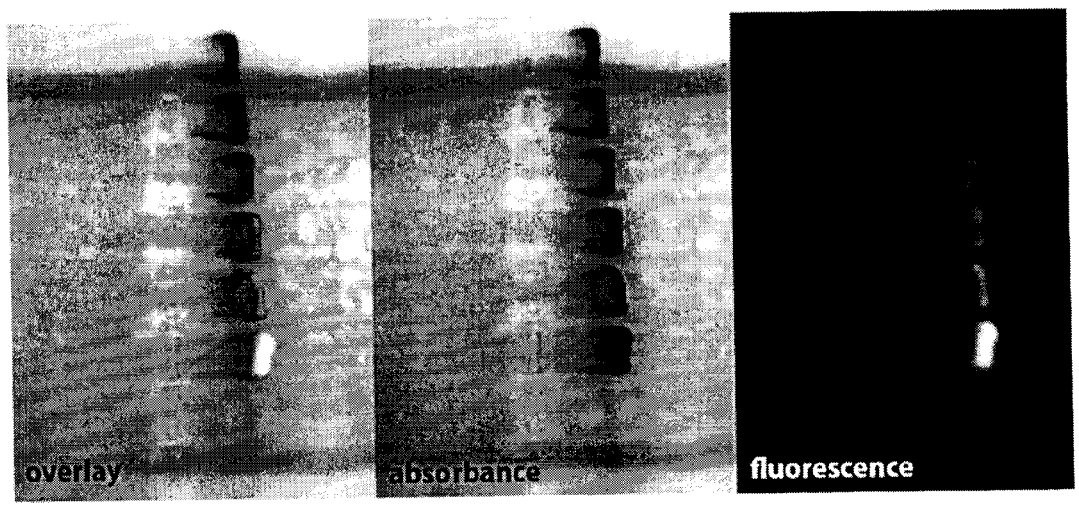
FIG. 3 shows the fluorescence signal arising from NP coated particles with a PEG spacer of 5000 kDa, equivalent to 5 nm with the brightness of the signal dependent upon the number of fluorophores coated onto the surface.

Particles having 0.1× biotin-PEG molecules per $nm^2$ were first synthesized. Streptavidin-A750 was mixed with the biotin-GNP by adding it in a small volume scintillation vial, 150 µl total volume in phosphate buffered saline (PBS). The streptavidin-A750 in 150 µl total PBS was then added while rapidly stirring the gold nanoparticles (GNP) solution. After incubating for 5 minutes, the product was centrifuged, and excess streptavidin was removed by washing. Biotin-transferrin was added to the streptavidin-coated nanoparticles. The product was then added to an agarose gel to test gel-shift by migration. Referring now to FIG. 2, from left to right is the fluorescence and white light overlay, then the white light only showing migration of the particles, and finally the fluorescence only channel. The left hand treatment is the particles prior to spinning and washing the excess streptavidin away. The middle column is the washed biotin-GNP, bound with streptavidin, then biotin-transferrin was added. The final column is the washed biotin-GNP with streptavidin added, but with no biotin-transferrin added. The two outer treatments shows that the streptavidin bound the biotin-GNP without causing cross-linking of the particles (no fluorescence is visible in the well of the left treatment, demonstrating that no cross-linking occurred, which would "aggregate" the particles and prevent migration). The right treatment shows that the washing procedure caused a small amount of particle aggregation, visible by the fluorescent particles stuck in the well. The middle column shows a greater degree of particle cross-linking by addition of the biotin-transferrin. It also shows a gel-shift due to addition of the biotin-transferrin to the particles. Overall, our results demonstrate that the streptavidin was successfully added to the GNP in a manner that did not cause cross linking and allowed binding of biotin-labelled biomolecules. The gel-shift proves this. A small amount of cross-linking may occur with the particles, which indicates that the number of biotin-labelled biomolecules added to the solution, the proportions of which, and also the method of adding and mixing can be optimized further to reduce cross linking and aggregation.

In final experiments, the addition of biotin-transferrin to the constructs of GNP-streptavidin was optimized. The volumes used for mixing, and the ratio of biotin-transferrin to GNP-streptavidin were examined. So were total signal, migration and cross-linking examined using gel electrophoresis. Once optimized, the ability of the constructs to bind their targets in an ELISA format was examined. Successful ELISA results indicated the labelling of gold nanoparticles with the protein transferrin by comparison the ELISA experiment of transferrin-coated gold nanoparticles with albumin-coated gold nanoparticles. The constructs were incubated in the wells, excess was washed off, and fluorescence resulting from specific binding was measured.

Final Product

Following the optimized protocol, biotin-GNP was synthesized and complexes of 3 fluorescently coloured nanoparticles were constructed, each having a different targeting molecule. Each different nanoparticle was able to specifically bind their respective targets, and did not bind non-specifically to other targets. The number of different fluorescent probes that can be constructed with this approach was limited by a) the number of commercially available fluorescently labelled streptavidins, or b) the number of possible fluorescently labeled streptavidin molecules, synthesized by covalent attachment of fluorophores to the streptavidin, and c) the number of biotin-targeting molecules available or d) the number of biotin-targeting molecules synthesized by conjugating biotin to a targeting molecule. For example, Invitrogen currently sells 40-50 variations of streptavidin labelled with fluorophores, and a number of quantum dot-conjugates of streptavidin that could be used. Because new fluorophores are constantly being developed, there is really no upper limit to the number of potential conjugates that could be used. Similarly, because biotin is readily conjugated to any targeting molecule of interest, there is an almost limitless variety of combinations of fluorophores and targeting molecules that can be combined on the present platform.

Assay Kit

This description also encompasses an assay kit of fluorescent, functionalized nanoparticles, with various components included in the kit, as well as a specific protocol for the end user to assemble the components. In broad terms there is provided an assay kit of fluorescent, functionalized noble metal nanoparticles comprising the following separate components:

Solution A comprising an aqueous solution of nanoparticles;

Solution B comprising a "conjugation buffer";

Solution C comprising streptavidin-fluorophore conjugate stock solutions in a conjugation buffer, each with a different fluorophore;

and instructions for assembling the components in accordance with the process as defined above for the production of fluorescent nanoparticles.

More specifically the kit may comprise the following components:

Solution A comprising a stock vial of concentrated nanoparticles in for example, aqueous solution;

Solution B comprising a "conjugation buffer" or more specifically a phosphate buffered saline plus surfactant such as 0.1% Tween 20™ (weight-to-volume);

Solution C comprising a number, for example 2 to 20, of streptavidin-fluorophore conjugate stock solutions in conjugation buffer, each with a different fluorophore;

A wash buffer, for example a phosphate buffered saline plus 0.5% Tween 20™ (w/v);

A binding buffer or phosphate buffered saline plus a surfactant such as 0.05% Tween 20™ (w/v); and A number of scintillation vials and stir bars to allow assembly.

The specific kit also contains a protocol for preparing the reagent. For example, the kit contains specific instructions for the end user such as:

1. Add a small volume (10 μL) of Solution A to 500 μl of Solution B in a 1.5 mL Eppendorf tube. Pipette this solution into an empty scintillation vial and stir rapidly on a magnetic stir plate.
2. Add a small volume (10 μL) of Solution C to 500 μL of Solution C in a 1.5 mL Eppendorf tube. Pipette this solution into the scintillation vial while stirring rapidly. Incubate 15 minutes at room temperature, while stirring.
3. Centrifuge the reaction for 3 minutes at 2000×g. Remove 900 μL of supernatant without disturbing the pellet. Add 900 μL of Wash Buffer, vortex to mix, and repeat centrifuge and wash a total of 3 times. Resuspend the pellet with 900 μL of Solution B.
4. Prepare a solution of the biotinylated targeting molecule (user provided) in Solution B, to a final concentration of 1 mg/mL.
5. Add 10 μL of the biotinylated targeting molecule to the nanoparticle solution and then incubate 30 minutes.
6. Repeat the wash step described in step 3, a total of 3 times. After the last wash, remove as much supernatant liquid as possible without disturbing the pellet. Resuspend the nanoparticles in 1 mL of Solution D.
7. The fluorescent, functionalized nanoparticles are now ready for use. Optimize the volume of nanoparticle reagent needed for your specific assay.

Most particularly there is provided particles synthesized on the nanometer scale that have many potential applications, for instance as biomedical devices (diagnostic and therapeutic agents). The present process optimizes the synthesis of fluorescent gold nanoparticles in particular, generally over the range of 10-100 nm. These particles have advantageous properties, including the ability to produce a wide range of particle sizes, highly stable particles both in vitro and in vivo, and the ability to use a variety of organic dyes (for example, any Alexa Fluor dye). Because of the flexibility to apply any fluorescent dye, the nanoparticle can have a wide range of fluorescent properties. The particles consist of a gold cluster core, a poly-(ethylene glycol) (PEG) outer brush layer, and a biotin linker presented on the outside of a proportion of the PEG layer that provides a rapid, easy means of attaching a fluorescence dye by biotin-avidin (or derivative of avidin) linkage. The materials used in synthesizing these fluorescent particles have previously been approved for internal use by the U.S. FDA. These particles are comparable in many ways to fluorescent nanocrystals, quantum dots. Fluorescent gold nanoparticles are considered to be applicable as a reagent including but not limited to in vitro cell labelling, in vitro diagnostic assay labelling, and in vivo tracking or tumor targeting.

All documents referenced herein are incorporated into this description by reference and in their entirety. It should be understood that the foregoing disclosure emphasizes certain specific embodiments of the invention and that all modifications or alternatives equivalent thereto are within the spirit and scope of the invention as set forth in the appended claims.

The invention claimed is:

1. A process for the production of noble metal or silica nanoparticles as probes capable to fluoresce to label cells and tissues, the method comprising:

(1) providing a platform of the nanoparticles;

(2) covering the surfaces of the nanoparticles to saturation with thiol-terminated polymers by one of the following methods:
  (a) mixing the nanoparticles with methoxy-(polyethylene glycol)-thiol, the methoxy-(polyethylene glycol)-thiol having a MW of about 10,000 atomic mass units (amu), and biotin-(polyethylene glycol)-thiol, the biotin-(polyethylene glycol)-thiol having a MW of about 10,000 amu;
  (b) mixing the nanoparticles with fluorescently-labeled methoxy-(polyethylene glycol)-thiol, the methoxy-(polyethylene glycol)-thiol having a MW of about 10,000 amu and biotin-(polyethylene glycol)-thiol, the biotin-(polyethylene glycol)-thiol having a MW of about 10,000 amu;
  (c) coordinating thiol and biotin thiol to the surfaces of the nanoparticles by a non-covalent bond; and
  (d) directly conjugating methoxy-thiol and biotin-thiol to the surfaces of the nanoparticles,
whereby the polymers bind to the surfaces of the nanoparticles as a brush layer via thiol particle coordination of the thiol ends so that the biotin or methoxy ends are free, thereby obtaining polymer-covered nanoparticles;
(3) homogeneously mixing the resulting polymer-covered nanoparticles with fluorophore labeled avidin or an avidin derivative thereof in proportions of 1 biotin molecule for every 10 to 1000 avidin molecules thereby obtaining fluorescent multi-coloured nanoparticle-avidin complexes and the fluorophore labeled avidin or a derivative thereof being spaced away from the surface of the noble metal or silica nanoparticles, thus reducing or removing the potential quenching of the fluorophore.

2. The process as claimed in claim 1 wherein the fluorophore is an organic fluorophore selected from the group comprising 2-[5-(1-{6-[(2,5-dioxopyrrolidin-1-yl)oxy]-6-oxohexyl}-3,3-dimethyl-5-sulfonato-1,3-dihydro-2H-indol-2-ylidene)penta-1,3-dien-1-yl]-1-ethyl-3,3-dimethyl-3H-indolium-5-sulfonate and fluorescein isothiocyanate and wherein the organic fluorophore is coated onto the surfaces of the polymer coatings of the nanoparticles via a polyethylene-thiol spacer.

3. The process of claim 1 wherein the distance between the fluorophore to the surface of the nanoparticle is from about 4 to about 15 nm.

4. The process as claimed in claim 1 wherein the nanoparticles are noble metal nanoparticles.

5. The process as claimed in claim 1 wherein the process further comprises adding biotinylated targeting molecules to the nanoparticle-avidin complexes, and wherein the targeting molecules are selected from antibodies, peptides and aptamers.

6. A process for the production of gold nanoparticles as probes capable to fluoresce to label cells and tissues, the method comprising:
(1) providing a platform of gold nanoparticles;
(2) covering the surfaces of the gold nanoparticles to saturation with thiol-terminated polymers by one of the following methods:
  (a) mixing the gold nanoparticles with methoxy-(polyethylene glycol)-thiol and biotin-(polyethylene glycol)-thiol;
  (b) coordinating thiol and biotin thiol to the surfaces of the gold nanoparticles by a non-covalent bond; and
  (c) directly conjugating methoxy-thiol and biotin-thiol to the surfaces of the gold nanoparticles,
whereby the polymers bind to the surfaces of the gold nanoparticles as a brush layer via thiol particle coordination of the thiol ends so that the biotin or methoxy ends are free, thereby obtaining polymer-covered gold nanoparticles; and
(3) homogeneously mixing the resulting polymer-covered gold nanoparticles with organic fluorophore labeled avidin or a derivative thereof in proportions of 1 biotin molecule for every 40 to 1000 avidin molecules thereby obtaining fluorescent multi-coloured gold nanoparticle-avidin complexes, fluorophore labeled avidin or a derivative thereof being spaced away from the gold nanoparticle surface, thus reducing or removing the potential quenching of the organic fluorophore.

* * * * *